United States Patent
Takahashi

(10) Patent No.: US 11,464,393 B2
(45) Date of Patent: Oct. 11, 2022

(54) ENDOSCOPE APPARATUS AND METHOD OF OPERATING ENDOSCOPE APPARATUS

(71) Applicant: OLYMPUS CORPORATION, Tokyo (JP)

(72) Inventor: Jumpei Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 265 days.

(21) Appl. No.: 16/810,139

(22) Filed: Mar. 5, 2020

(65) Prior Publication Data
US 2020/0196833 A1    Jun. 25, 2020

Related U.S. Application Data

(63) Continuation of application No. PCT/JP2017/033033, filed on Sep. 13, 2017.

(51) Int. Cl.
*A61B 1/00* (2006.01)
*A61B 1/045* (2006.01)
*A61B 1/06* (2006.01)

(52) U.S. Cl.
CPC ........ *A61B 1/00009* (2013.01); *A61B 1/0002* (2013.01); *A61B 1/045* (2013.01); *A61B 1/0638* (2013.01); *A61B 1/0646* (2013.01); *A61B 1/0653* (2013.01); *A61B 1/0684* (2013.01)

(58) Field of Classification Search
CPC .... A61B 1/0002; A61B 1/0646; A61B 1/0653
See application file for complete search history.

(56) References Cited

U.S. PATENT DOCUMENTS 10,039,439 B2 * 8/2018 Aoyama ................. A61B 1/044
10,052,015 B2 * 8/2018 Shiraishi ............... G06T 7/0012
(Continued)

FOREIGN PATENT DOCUMENTS

EP    2368488 A1    9/2011
EP    2850994 A1    3/2015
(Continued)

OTHER PUBLICATIONS

International Search Report dated Nov. 21, 2017 issued in PCT/JP2017/033033.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope apparatus includes a light source apparatus, an image processing circuit configured to subject a first image or a second image obtained by irradiating first or second narrow band light to predetermined image processing and output the image, and a control circuit configured to perform control to acquire signal intensity information about a signal intensity of the image pickup signal outputted from the image pickup device in response to irradiation with the first narrow band light based on a current operation state of a light source configured to generate first narrow band light and further maintain a ratio of respective brightnesses of the first image and the second image used for generating the observation image to be a predetermined ratio based on the signal intensity information.

10 Claims, 4 Drawing Sheets

(56) References Cited

U.S. PATENT DOCUMENTS

| | | | | |
|---|---|---|---|---|
| 2003/0060684 A1* | 3/2003 | Ayame | A61B 1/0655 | 600/168 |
| 2008/0165248 A1* | 7/2008 | Wang | A61B 1/00057 | 348/76 |
| 2008/0306343 A1* | 12/2008 | Yamazaki | A61B 1/000095 | 600/180 |
| 2009/0036743 A1* | 2/2009 | Yabe | A61B 1/00186 | 600/180 |
| 2009/0137873 A1* | 5/2009 | Mitsuhashi | A61B 1/0004 | 600/118 |
| 2011/0237885 A1 | 9/2011 | Matsubara | | |
| 2012/0053434 A1* | 3/2012 | Saito | A61B 1/063 | 600/324 |
| 2012/0075458 A1* | 3/2012 | Kino | H04N 7/183 | 348/81 |
| 2012/0078044 A1* | 3/2012 | Yamaguchi | H04N 5/2354 | 600/109 |
| 2013/0006109 A1* | 1/2013 | Takei | A61B 1/00009 | 600/432 |
| 2013/0039562 A1* | 2/2013 | Watanabe | A61B 1/0638 | 382/167 |
| 2013/0096376 A1* | 4/2013 | Takei | A61B 1/043 | 600/103 |
| 2013/0150728 A1* | 6/2013 | Takei | A61B 1/045 | 600/476 |
| 2013/0265401 A1* | 10/2013 | Igarashi | A61B 1/000094 | 348/68 |
| 2013/0286175 A1* | 10/2013 | Hashimoto | A61B 1/000095 | 348/68 |
| 2014/0125231 A1* | 5/2014 | Nishio | G02B 23/2461 | 315/131 |
| 2014/0218479 A1* | 8/2014 | Nishimura | A61B 1/00009 | 348/46 |
| 2014/0272765 A1* | 9/2014 | Andreiko | A61B 1/253 | 433/29 |
| 2015/0087903 A1* | 3/2015 | Kuramoto | A61B 1/00059 | 600/109 |
| 2015/0105614 A1* | 4/2015 | Igarashi | A61B 1/0646 | 600/104 |
| 2015/0105758 A1* | 4/2015 | Igarashi | A61B 1/0638 | 606/3 |
| 2015/0105769 A1* | 4/2015 | Igarashi | A61B 17/083 | 607/88 |
| 2015/0146931 A1* | 5/2015 | Maricic | G06T 7/90 | 382/106 |
| 2015/0212312 A1* | 7/2015 | Hopkins | A61B 1/0661 | 250/504 R |
| 2016/0015247 A1* | 1/2016 | Irion | A61B 1/00059 | 600/109 |
| 2016/0206185 A1* | 7/2016 | Kinouchi | H04B 10/25 | |
| 2016/0353540 A1* | 12/2016 | Merkt | A61B 1/0655 | |
| 2017/0027428 A1* | 2/2017 | Igarashi | G02B 23/2461 | |
| 2018/0289240 A1* | 10/2018 | Aoyama | A61B 1/04 | |
| 2019/0068864 A1* | 2/2019 | Ohashi | A61B 1/044 | |
| 2019/0324253 A1* | 10/2019 | Zapata | G06T 7/0012 | |
| 2020/0260940 A1* | 8/2020 | Kutsuma | A61B 1/0661 | |
| 2021/0007578 A1* | 1/2021 | Aoyama | A61B 1/00186 | |
| 2021/0052153 A1* | 2/2021 | Morita | A61B 1/042 | |

FOREIGN PATENT DOCUMENTS

| | | |
|---|---|---|
| JP | 2011-200410 A | 10/2011 |
| JP | 5355827 B1 | 11/2013 |
| JP | 2015-061569 A | 4/2015 |
| JP | 5974204 B1 | 8/2016 |

* cited by examiner

| CURRENT VALUE CV (AMP) | SIGNAL OUTPUT RATIO SR |
|---|---|
| CVA | SRA |
| CVB | SRB |
| CVC | SRC |
| ⋮ | ⋮ |
| CVM | 1.0 |

TD

| CURRENT VALUE CW (AMP) | SIGNAL OUTPUT RATIO SS |
|---|---|
| CWA | SSA |
| CWB | SSB |
| CWC | SSC |
| ⋮ | ⋮ |
| CWM | 1.0 |

TE

ENDOSCOPE APPARATUS AND METHOD OF OPERATING ENDOSCOPE APPARATUS

CROSS REFERENCE TO RELATED APPLICATION

This application is a continuation application of PCT/JP2017/033033 filed on Sep. 13, 2017, the entire contents of which are incorporated herein by this reference.

BACKGROUND OF THE INVENTION

1. Field of the Invention

The present invention relates to an endoscope apparatus and a method of operating the endoscope apparatus.

2. Description of the Related Art

In endoscope observation in a medical field, an observation method of irradiating a living tissue with narrow-band light having a center wavelength (wavelength band) set depending on a light absorption characteristic of hemoglobin to visualize a blood vessel existing at a desired depth of the living tissue has been conventionally proposed.

More specifically, Japanese Patent No. 5974204 discloses a configuration in which a living mucous membrane is irradiated with narrow band light in the vicinity of 600 nm as light that is relatively easy to absorb in hemoglobin and narrow band light in the vicinity of 630 nm as light that is relatively difficult to absorb in hemoglobin to together visualize a blood vessel existing at a depth of the living mucous membrane and a contour of a background portion leading to the depth from a surface layer of the living mucous membrane. Japanese Patent No. 5974204 discloses a configuration related to a light source apparatus including an LED configured to generate narrow band light in the vicinity of 600 nm and an LED configured to generate narrow band light in the vicinity of 630 nm.

In the above-described observation method, a semiconductor light source such as an LED or an LD (laser diode) has been generally used as a light source configured to generate narrow band light. However, when the semiconductor light source is used in the above-described observation method, there can occur a situation where an image having a different color tone from an original color tone is displayed due to a center wavelength (wavelength band) of narrow band light to be emitted from the semiconductor light source shifting from an original center wavelength (wavelength band).

SUMMARY OF THE INVENTION

According to an aspect of the present invention, there is provided an endoscope apparatus including a light source apparatus configured to sequentially or simultaneously generate as illumination light first narrow band light as light having an intensity within a predetermined wavelength range of a red range in which a light absorption coefficient in a light absorption characteristic of hemoglobin sharply changes and second narrow band light as light having an intensity on the side of a longer wavelength than the predetermined wavelength range, an image pickup device configured to pick up an image of return light from an object including a region containing hemoglobin irradiated with the illumination light and output an image pickup signal, an image processing circuit configured to subject at least one of a first image obtained by performing image pickup of the return light from the object irradiated with the first narrow band light and a second image obtained by performing image pickup of the return light from the object irradiated with the second narrow band light to predetermined image processing and output at least one of the first image and the second image subjected to the predetermined image processing, an observation image generation circuit configured to generate an observation image using the first image and the second image obtained as a processing result of the predetermined image processing and output the generated observation image to a display apparatus, and a control circuit configured to perform control to acquire signal intensity information as information about a signal intensity of the image pickup signal outputted from the image pickup device in response to irradiation of the object with the first narrow band light based on a detection result obtained by detecting a predetermined parameter representing a current operation state of a predetermined light source corresponding to a generation source of the first narrow band light in the light source apparatus and further maintain a ratio of respective brightnesses of the first image and the second image used for generating the observation image to be a predetermined ratio based on the signal intensity information.

According to another aspect of the present invention, there is provided an endoscope apparatus including a light source apparatus configured to sequentially or simultaneously generate as illumination light first narrow band light as light having an intensity within a predetermined wavelength range of a red range in which a light absorption coefficient in a light absorption characteristic of hemoglobin sharply changes, second narrow band light as light having an intensity on the side of a longer wavelength than the predetermined wavelength range, and third narrow band light having an intensity outside the predetermined wavelength range and having an intensity in either one of a blue range and a green range, an image pickup device configured to pick up an image of return light from an object including a region containing hemoglobin irradiated with the illumination light and output an image pickup signal, an image processing circuit configured to subject at least one of a first image obtained by performing image pickup of the return light from the object irradiated with the first narrow band light, a second image obtained by performing image pickup of the return light from the object irradiated with the second narrow band light, and a third image obtained by performing image pickup of the return light from the object irradiated with the third narrow band light to predetermined image processing and output at least one of the first image, the second image and the third image subjected to the predetermined image processing, an observation image generation circuit configured to generate an observation image using the first image, the second image, and the third image obtained as a processing result of the predetermined image processing and output the generated observation image to a display apparatus, and a control circuit configured to perform control to acquire signal intensity information as information about a signal intensity of the image pickup signal outputted from the image pickup device in response to irradiation of the object with the first narrow band light based on a detection result obtained by detecting one or more predetermined parameter representing a current operation state of a predetermined light source corresponding to a generation source of the first narrow band light in the light source apparatus and further maintain a ratio of respective brightnesses of the first image, the second image, and the third image used for generating the observation image to be a predetermined ratio based on the signal intensity information.

According to still another aspect of the present invention, there is provided a method of operating an endoscope apparatus, the method including sequentially or simultaneously generating as illumination light first narrow band light as light having an intensity within a predetermined wavelength range of a red range in which a light absorption coefficient in a light absorption characteristic of hemoglobin sharply changes and second narrow band light as light having an intensity on the side of a longer wavelength than the predetermined wavelength range, picking up an image of return light from an object including a region containing hemoglobin irradiated with the illumination light and output an image pickup signal, subjecting at least one of a first image obtained by performing image pickup of the return light from the object irradiated with the first narrow band light and a second image obtained by performing image pickup of the return light from the object irradiated with the second narrow band light to predetermined image processing and outputting at least one of the first image and the second image subjected to the predetermined image processing, generating an observation image using the first image and the second image obtained as a processing result of the predetermined image processing and outputting the generated observation image to a display apparatus, acquiring signal intensity information as information about a signal intensity of the image pickup signal in response to irradiation of the object with the first narrow band light based on a detection result of a predetermined parameter representing a current operation state of a predetermined light source corresponding to a generation source of the first narrow band light, and performing control to maintain a ratio of respective brightnesses of the first image and the second image used for generating the observation image to be a predetermined ratio based on the signal intensity information.

DETAILED DESCRIPTION OF THE PREFERRED EMBODIMENT(S)

An embodiment of the present invention will be described below with reference to the drawings.

Figure 1:
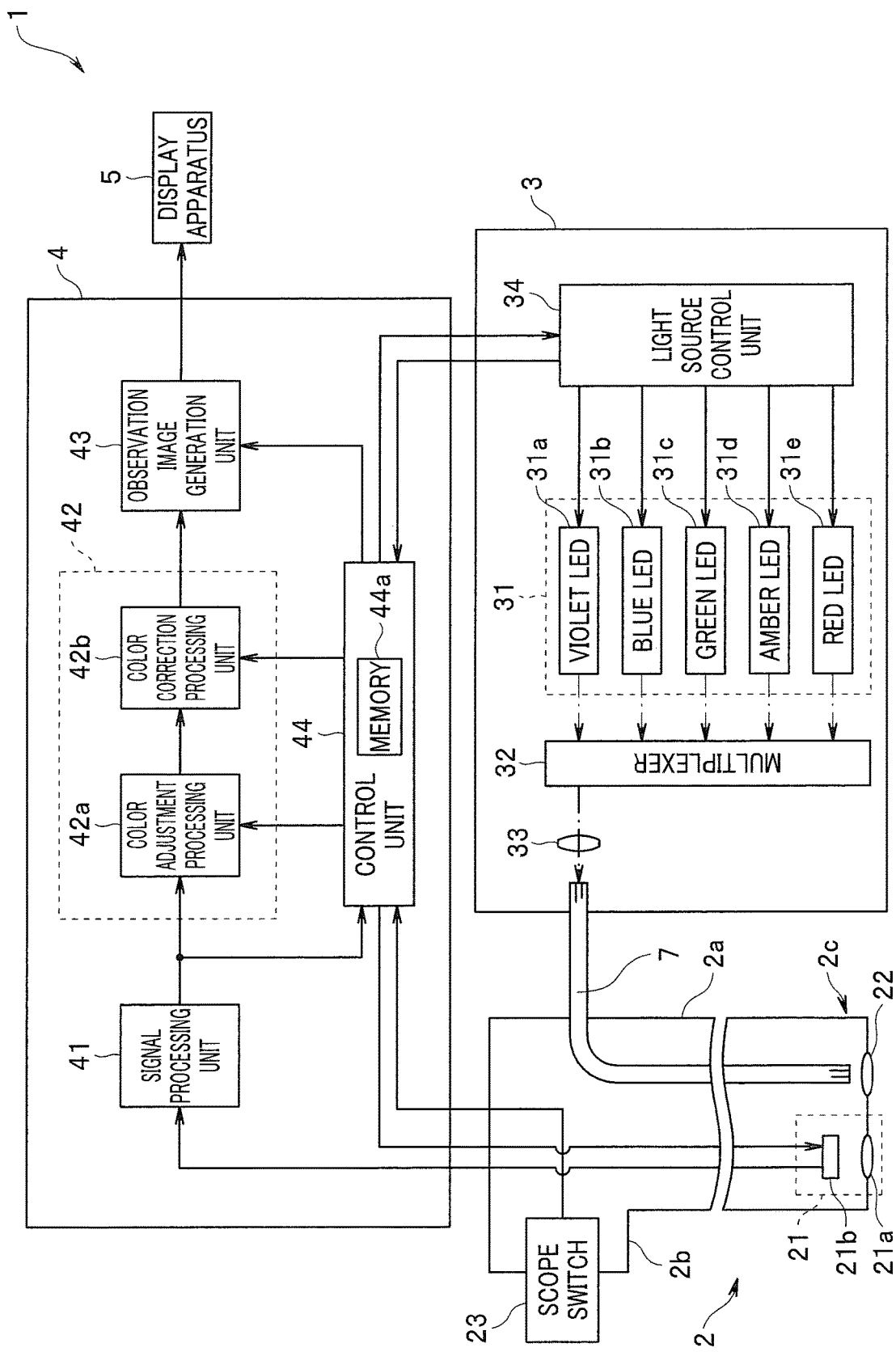
FIG. 1 is a diagram illustrating a configuration of a principal part of an endoscope apparatus according to an embodiment.

An endoscope apparatus 1 includes an endoscope 2 configured to be insertable into a subject and pick up an image of an object such as a living tissue existing within the subject and output an image pickup signal, a light source apparatus 3 configured to supply illumination light used to observe the object via a light guide 7 arranged to be inserted into the endoscope 2, a processor 4 configured to generate and output an observation image or the like corresponding to the image pickup signal to be outputted from the endoscope 2, and a display apparatus 5 configured to display on a screen the observation image to be outputted from the processor 4, as illustrated in FIG. 1. FIG. 1 is a diagram illustrating a configuration of a principal part of the endoscope apparatus according to the embodiment.

The endoscope 2 includes an insertion section 2a formed in an elongated shape insertable into the subject and an operation section 2b provided on a proximal end side of the insertion section 2a. The endoscope 2 is configured to be detachably connected to the processor 4 via a universal cable (not illustrated) containing a signal line used for transmitting various signals such as an image pickup signal to be outputted from an image pickup unit 21 (described below), for example. The endoscope 2 is configured to be detachably connected to the light source apparatus 3 via a light guide cable (not illustrated) containing at least a part of the light guide 7.

A distal end portion 2c of the insertion section 2a is provided with an image pickup unit 21 configured to pick up an image of the object such as the living tissue within the subject, an emission end portion of the light guide 7, and an illumination optical system 22 configured to irradiate the object with the illumination light transmitted via the light guide 7.

The image pickup unit 21 is configured to pick up an image of return light from the object irradiated with the illumination light from the illumination optical system 22 and output an image pickup signal. More specifically, the image pickup unit 21 includes an objective optical system 21a configured to form an image of return light emitted from the object irradiated with the illumination light from the illumination optical system 22 and an image pickup device 21b configured by disposing a plurality of pixels for receiving and picking up an image of the return light in a matrix shape to match an image-forming position of the objective optical system 21a.

The image pickup device 21b is configured to include an image sensor such as a CCD or a CMOS. The image pickup device 21b is configured to perform an operation corresponding to a control signal to be outputted from the processor 4. The image pickup device 21b is configured to generate an image pickup signal by performing image pickup of return light formed by the objective optical system 21a and output the generated image pickup signal to the processor 4.

The operation section 2b is configured to have a shape that can be grasped by a user to operate. The operation section 2b is provided with a scope switch 23 configured to include one or more switches capable of issuing an instruction corresponding to an input operation of the user to the processor 4. More specifically, the scope switch 23 is configured to include an observation mode changeover switch (not illustrated) capable of issuing an instruction to set (switch) an observation mode of the endoscope apparatus 1 to either one of a white light observation mode and a special light observation mode in response to a user's operation, for example.

The light source apparatus 3 is configured to include a light emitting unit 31, a multiplexer 32, a light collecting lens 33, and a light source control unit 34.

The light emitting unit 31 is configured to include a violet LED 31a, a blue LED 31b, a green LED 31c, an amber LED 31d, and a red LED 31e. In other words, the light emitting unit 31 is configured to include a plurality of semiconductor light sources.

Figure 2:
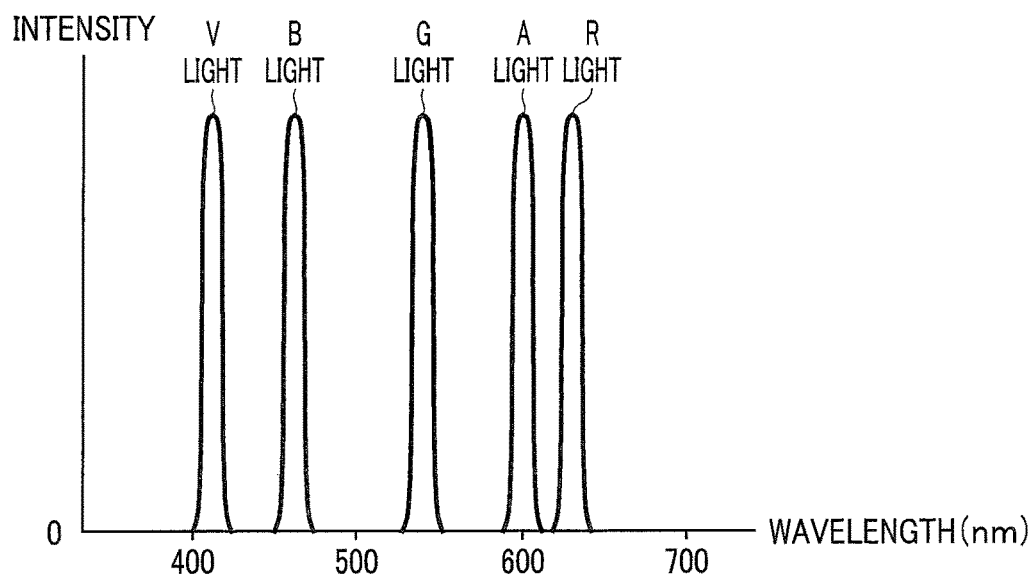
FIG. 2 is a diagram illustrating an example of a wavelength band of light to be emitted from each of LEDs provided in a light source apparatus according to the embodiment.
Figure 3:
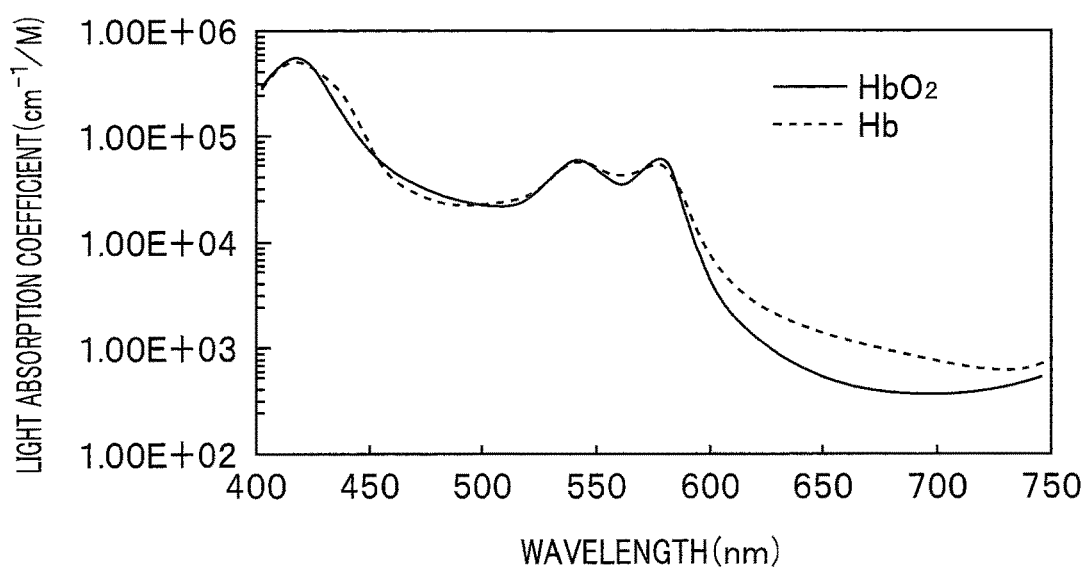
FIG. 3 is a diagram illustrating respective light absorption characteristics of oxygenated hemoglobin and reduced hemoglobin.

The violet LED 31a is configured to generate violet narrow band light (hereinafter referred to as V light). More specifically, the violet LED 31a is configured to generate as the V light light having a center wavelength set to the vicinity of 410 nm and having a bandwidth set to approximately 20 nm, as illustrated in FIG. 2, for example. In other words, the V light to be emitted from the violet LED 31a has an intensity within a predetermined wavelength range in which a light absorption coefficient in a blue range in a light absorption characteristic of hemoglobin (oxygenated hemoglobin and/or reduced hemoglobin) illustrated in FIG. 3 sharply changes. The violet LED 31a is configured to emit light or quench light in response to control by the light source control unit 34. The violet LED 31a is configured to generate V light having a light emission amount corresponding to the control by the light source control unit 34. FIG. 2 is a diagram illustrating an example of a wavelength band of light to be emitted from each of the LEDs provided in the light source apparatus according to the embodiment. FIG. 3 is a diagram illustrating respective light absorption characteristics of oxygenated hemoglobin and reduced hemoglobin.

The blue LED 31b is configured to generate blue narrow band light (hereinafter referred to as B light). More specifically, the blue LED 31b is configured to generate as the B light light having a center wavelength set to the vicinity of 460 nm and having a bandwidth set to approximately 20 nm, as illustrated in FIG. 2, for example. In other words, the B light to be emitted from the blue LED 31b has an intensity in a blue range on the side of a longer wavelength than the wavelength of the V light. The B light to be emitted from the blue LED 31b has an intensity outside a predetermined wavelength range in which a light absorption coefficient in the light absorption characteristic of hemoglobin illustrated in FIG. 3 sharply changes. The blue LED 31b is configured to emit light or quench light in response of control by the light source control unit 34. The blue LED 31b is configured to generate B light having a light emission amount corresponding to the control by the light source control unit 34.

The green LED 31c is configured to generate green narrow band light (hereinafter referred to as G light). More specifically, the green LED 31c is configured to generate as the G light light having a center wavelength set to the vicinity of 540 nm and having a bandwidth set to approximately 20 nm, as illustrated in FIG. 2, for example. In other words, the G light to be emitted from the green LED 31c has an intensity in a green range on the side of a longer wavelength than the wavelength of the V light (and the B light). The G light to be emitted from the green LED 31c has an intensity outside a predetermined wavelength range in which a light absorption coefficient in the absorption characteristic of hemoglobin illustrated in FIG. 3 sharply changes. The green LED 31c is configured to emit light or quench light in response to control by the light source control unit 34. The green LED 31c is configured to generate G light having a light emission amount corresponding to the control by the light source control unit 34.

The amber LED 31d is configured to generate amber narrow band light (hereinafter referred to as A light). More specifically, the amber LED 31d is configured to generate as the A light light having a center wavelength set to the vicinity of 600 nm and having a bandwidth set to approximately 20 nm, as illustrated in FIG. 2, for example. In other words, the A light to be emitted from the amber LED 31d has an intensity within a predetermined wavelength range in which a light absorption coefficient in a red range in the light absorption characteristic of hemoglobin illustrated in FIG. 3 sharply changes. The amber LED 31d is configured to emit light or quench light in response to control by the light source control unit 34. The amber LED 31d is configured to generate A light having a light emission amount corresponding to the control by the light source control unit 34.

The red LED 31e is configured to generate red narrow band light (hereinafter referred to as R light). More specifically, the red LED 31e is configured to generate as the R light light having a center wavelength set to the vicinity of 630 nm and having a bandwidth set to approximately 20 nm, as illustrated in FIG. 2, for example. In other words, the R light to be emitted from the red LED 31e has an intensity in a red range on the side of a longer wavelength than the wavelength of the A light. The R light to be emitted from the red LED 31e has an intensity outside a predetermined wavelength range in which a light absorption coefficient in the light absorption characteristic of hemoglobin illustrated in FIG. 3 sharply changes. The red LED 31e is configured to emit light or quench light in response to control by the light source control unit 34. The red LED 31e is configured to generate R light having a light emission amount corresponding to the control by the light source control unit 34.

The multiplexer 32 is configured to be able to multiplex lights emitted from the light emitting unit 31 and make the multiplexed lights incident on the light collecting lens 33.

The light collecting lens 33 is configured to collect the lights incident via the multiplexer 32 and emit the collected lights to the light guide 7.

The light source control unit 34 is configured to include a drive circuit and a control circuit, for example. The light source control unit 34 is configured to be able to supply a current required to operate each of the LEDs in the light emitting unit 31. The light source control unit 34 is configured to operate each of the LEDs in the light emitting unit 31 in response to the control signal to be outputted from the processor 4.

According to the above-described configuration, the light emitting unit 31 is configured to be able to sequentially or simultaneously generate as illumination light first narrow band light as light having an intensity within a predetermined wavelength range in which a light absorption coefficient in the light absorption characteristic of hemoglobin sharply changes, second narrow band light as light having an intensity outside the predetermined wavelength range, and third narrow band light as light having an intensity outside the predetermined wavelength range and different from the second narrow band light in response to the control by the light source control unit 34.

The processor 4 is configured to include a signal processing unit 41, an image processing unit 42, an observation image generation unit 43, and a control unit 44.

The signal processing unit 41 is configured to include a signal processing circuit, for example. The signal processing unit 41 is configured to subject the image pickup signal to be outputted from the endoscope 2 to predetermined signal processing such as A/D conversion to generate image data and output the generated image data to each of the image processing unit 42 and the control unit 44.

The image processing unit 42 is configured to include an image processing circuit, for example. The image processing unit 42 is configured to subject the image data to be outputted from the signal processing unit 41 to predetermined image processing and output the image data to the observation image generation unit 43. The image processing unit 42 is configured to include a color adjustment processing unit 42a and a color correction processing unit 42b, for example.

The color adjustment processing unit 42a is configured to subject the image data to be outputted via the signal processing unit 41 to color adjustment processing in response to the control signal to be outputted from the control unit 44, and output the image data which has been subjected to the color adjustment processing to the color correction processing unit 42b. Note that a specific example of color adjustment processing to be performed in the color adjustment processing unit 42a will be described below.

The color correction processing unit 42b is configured to subject the image data to be outputted via the color adjustment processing unit 42a to color correction processing in response to the control signal to be outputted from the control unit 44, and output the image data which has been subjected to the color correction processing to the observation image generation unit 43. Note that a specific example of color correction processing to be performed in the color correction processing unit 42b will be described below.

The observation image generation unit 43 is configured to include an image generation circuit, for example. The observation image generation unit 43 is configured to assign image data respectively having color components to be outputted via the image processing unit 42 to an R (red) channel, a G (green) channel, and a B (blue) channel of the display apparatus 5 in response to the control signal to be outputted from the control unit 44 to generate an observation image and output the generated observation image to the display apparatus 5. In other words, the observation image generation unit 43 is configured to generate an observation image using the image data respectively having the color components obtained as a result of predetermined image processing by the image processing unit 42 and output the generated observation image to the display apparatus.

The control unit 44 is configured to include a control circuit, for example. The control unit 44 is configured to generate and output a control signal for performing an operation corresponding to an observation mode of the endoscope apparatus 1 based on an instruction issued in the observation mode changeover switch in the scope switch 23. The control unit 44 is configured to generate and output a control signal for controlling the operation of the image pickup device 21b. The control unit 44 is configured to generate and output a control signal for controlling the operation of each of the LEDs in the light emitting unit 31 via the light source control unit 34.

The control unit 44 is configured to include a memory 44a storing one or more table data (described below). The control unit 44 is configured to perform brightness detection processing for detecting a current brightness in the observation mode set in the scope switch 23 based on the image data to be outputted from the signal processing unit 41. The control unit 44 is configured to generate a control signal for performing a light-adjusting operation to bring the current brightness obtained as a processing result of the above-described brightness detection processing closer to a predetermined brightness target value and output the generated control signal to the light source control unit 34. The control unit 44 is configured to be able to detect respective current values of magnitudes of currents (hereinafter also referred to as present current values) being supplied to each of the LEDs in the light emitting unit 31 from the light source control unit 34 with the above-described light-adjusting operation. The control unit 44 is configured to refer to the table data read from the memory 44a when the observation mode of the endoscope apparatus 1 is set to the special light observation mode to acquire a signal output ratio (described below) corresponding to a detection result of the present current value being supplied to the predetermined LED in the light emitting unit 31 from the light source control unit 34 with the above-described light-adjusting operation, and output a control signal including the acquired signal output ratio to each of the color adjustment processing unit 42a and the color correction processing unit 42b.

Note that in the present embodiment, the light source control unit 34 is desirably provided with a lag-lead filter or the like configured to have a time constant for defining an operation interval of the above-described light-adjusting operation, for example, to avoid occurrence of hunching caused by the light-adjusting operation.

In the present embodiment, each of the units in the processor 4 may be configured as individual electronic circuit, or may be configured as a circuit block in an integrated circuit such as an FPGA (field programmable gate array). In the present embodiment, the processor 4 may be configured to include one or more CPUs, for example. In the present embodiment, the control unit 44 may cause a computer to perform an operation, processing, and the like corresponding to a function of each of the units in the processor 4 by reading and executing a program stored in the memory 44a, for example.

The display apparatus 5 includes an LCD (liquid crystal display), for example, and is configured to be able to display the observation image or the like to be outputted from the processor 4.

Then, the function of the present embodiment will be described below.

A user such as an operator connects the units in the endoscope apparatus 1 to one another to turn on power, and then operates the observation mode changeover switch in the scope switch 23, to issue an instruction to set the observation mode of the endoscope apparatus 1 to the white light observation mode.

A specific example of an operation of each of the units performed when the observation mode of the endoscope apparatus 1 is set to the white light observation mode will be described below.

The control unit 44 generates a control signal for sequentially emitting the B light, the G light, and the R light from the light source apparatus 3 and outputs the generated control signal to the light source control unit 34 when detecting that the instruction to set the observation mode of the endoscope apparatus 1 to the white light observation mode has been issued. The control unit 44 generates a control signal for performing an operation corresponding to the white light observation mode and outputs the generated control signal to the color adjustment processing unit 42a, the color correction processing unit 42b, and the observation image generation unit 43 when detecting that the instruction to set the observation mode of the endoscope apparatus 1 to the white light observation mode has been issued.

The light source control unit 34 subjects the light emitting unit 31 to control to cause the blue LED 31b, the green LED 31c, and the red LED 31e to repeatedly emit lights in this order while causing the violet LED 31a and the amber LED 31d to quench lights, for example, in the white light observation mode in response to the control signal to be outputted from the control unit 44. The B light, the G light, and the R light are sequentially irradiated as illumination light onto the object in response to such an operation of the light source control unit 34, and an image pickup signal generated by performing image pickup of return light of the illumination light is sequentially outputted from the image pickup device 21b to the signal processing unit 41.

The signal processing unit 41 subjects the image pickup signal to be sequentially outputted from the image pickup device 21b to predetermined signal processing, to generate image data PB as image data having a blue component obtained by performing image pickup of return light from the object irradiated with the B light, image data PG as image data having a green component obtained by performing image pickup of return light from the object irradiated with the G light, and image data PR as image data having a red component obtained by performing image pickup of return light from the object irradiated with the R light and output the generated image data to each of the image processing unit 42 and the control unit 44.

The control unit 44 performs brightness detection processing for detecting a current brightness WCB in the white light observation mode based on the image data respectively having the color components to be outputted from the signal processing unit 41.

More specifically, the control unit 44 performs processing for calculating an average value of respective pixel values of pixels included in each of the image data PB, PG, and PR to be outputted from the signal processing unit 41, and detecting the calculated average value as the current brightness WCB in the white light observation mode, for example, as the above-described brightness detection processing. Note that the control unit 44 may perform processing for detecting either one of a weighted average value of the respective pixel values of the pixels included in each of the image data PB, PG, and PR to be outputted from the signal processing unit 41 and the average value of the respective pixel values of the pixels included in the image data having a predetermined color component to be outputted from the signal processing unit 41 as the current brightness WCB in the white light observation mode, for example. The control unit 44 may use an entire area of the image data to be outputted from the signal processing unit 41 as a processing target or may use only a partial region included in the image data to be outputted from the signal processing unit 41 as a processing target when performing the above-described brightness detection processing.

The control unit 44 generates a control signal for performing a light-adjusting operation for bringing the current brightness WCB obtained as a processing result of the above-described brightness detection processing closer to a brightness target value WTB in the white light observation mode and outputs the generated control signal to the light source control unit 34.

More specifically, the control unit 44 generates a control signal for performing a light-adjusting operation for bringing a ratio of the current brightness WCB to the brightness target value WTB (WCB/WTB) closer to 1 and outputs the generated control signal to the light source control unit 34, for example.

According to the operation of the control unit 44 as described above, the B light, the G light, and the R light each having a light amount suitable for white light observation are supplied as illumination light to the endoscope 2 from the light source apparatus 3.

The color adjustment processing unit 42a subjects the image data respectively having the color components to be outputted via the signal processing unit 41 to white balance adjustment processing, and outputs the image data respectively having the color components which have been subjected to the white balance adjustment processing to the color correction processing unit 42b, for example, in the white light observation mode in response to the control signal to be outputted from the control unit 44.

The color correction processing unit 42b subjects the image data respectively having the color components to be outputted via the color adjustment processing unit 42a to gamma correction processing, and outputs the image data respectively having the color components which have been subjected to the gamma correction processing to the observation image generation unit 43, for example, in the white light observation mode in response to the control signal to be outputted from the control unit 44.

The observation image generation unit 43 generates a white light observation image by assigning the image data PB to be outputted via the color correction processing unit 42b to the B channel of the display apparatus 5, assigning the image data PG to be outputted via the color correction processing unit 42b to the G channel of the display apparatus 5, and assigning the image data PR to be outputted via the color correction processing unit 42b to the R channel of the display apparatus 5 and outputs the generated white light observation image to the display apparatus 5, for example, in the white light observation mode in response to the control signal to be outputted from the control unit 44.

According to the operation of each of the units as described above, when the observation mode of the endoscope apparatus 1 is set to the white light observation mode, a white light observation image having substantially the same color tone as a color tone when the object such as the living tissue is viewed with naked eyes is displayed on the display apparatus 5, for example.

The user inserts the insertion section 2a into a body cavity of an examinee while confirming the white light observation image to be displayed on the display apparatus 5 with the observation mode of the endoscope apparatus 1 set to the white light observation mode, and arranges the distal end portion 2c at a position where a desired object (living tissue) existing within the body cavity enters an observation field of view of the objective optical system 21a. Then, the user operates the observation mode changeover switch in the scope switch 23, to issue an instruction to set the observation mode of the endoscope apparatus 1 to the special light observation mode.

A specific example of the operation of each of the units performed when the observation mode of the endoscope apparatus 1 is set to the special light observation mode will be described below. A case where the wavelength band of the A light to be emitted from the amber LED 31d shifts toward a shorter wavelength from an original wavelength band will be described below as an example.

The control unit 44 generates a control signal for sequentially emitting the G light, the A light, and the R light from the light source apparatus 3 and outputs the generated control signal to the light source control unit 34 when detecting that an instruction to set the observation mode of the endoscope apparatus 1 to the special light observation mode has been issued.

The light source control unit 34 subjects the light emitting unit 31 to control to cause the green LED 31c, the amber LED 31d, and the red LED 31e to repeatedly emit lights in this order while causing the violet LED 31a and the blue LED 31b to quench lights, for example, in the special light observation mode in response to the control signal to be outputted from the control unit 44. The G light, the A light, and the R light are sequentially irradiated as illumination light onto the object, and an image pickup signal generated by performing image pickup of return light of the illumination light is sequentially outputted to the signal processing unit 41 from the image pickup device 21b in response to such an operation of the light source control unit 34. In other words, the image pickup unit 21 in the present embodiment picks up an image of return light from an object including a region containing hemoglobin illuminated with the G light, the A light, and the R light and outputs an image pickup signal in the special light observation mode.

The signal processing unit 41 subjects the image pickup signal to be sequentially outputted from the image pickup device 21b to predetermined signal processing, to generate the image data PG, image data PA as image data having an amber component obtained by performing image pickup of return light from the object irradiated with the A light, and the image data PR and output the generated image data to each of the image processing unit 42 and the control unit 44.

The control unit 44 performs brightness detection processing for detecting a current brightness SCB in the special light observation mode based on the image data respectively having the color components to be outputted from the signal processing unit 41.

More specifically, the control unit 44 performs processing for calculating an average value of respective pixel values of pixels included in each of the image data PG, PA, and PR to be outputted from the signal processing unit 41, and detecting the calculated average value as the current brightness SCB in the special light observation mode, for example, as the above-described brightness detection processing. Note that the control unit 44 may perform processing for detecting either one of a weighted average value of the respective pixel values of the pixels included in each of the image data PG, PA, and PR to be outputted from the signal processing unit 41 and the average value of the respective pixel values of the pixels included in the image data PA to be outputted from the signal processing unit 41 as the current brightness SCB in the special light observation mode, for example, as the above-described brightness detection processing. The control unit 44 may use an entire area of the image data to be outputted from the signal processing unit 41 as a processing target or may use a partial region of the image data to be outputted from the signal processing unit 41 as a processing target when performing the above-described brightness detection processing.

The control unit 44 generates a control signal for performing a light-adjusting operation to bring the current brightness SCB obtained as a processing result of the above-described brightness detection processing closer to a brightness target value STB in the special light observation mode and outputs the generated control signal to the light source control unit 34. More specifically, the control unit 44 generates a control signal for performing a light-adjusting operation to bring a ratio of the current brightness SCB to the brightness target value STB (SCB/STB) closer to 1 and outputs the generated control signal to the light source control unit 34, for example. In other words, according to such a light-adjusting operation, a current value of a current to be supplied to the amber LED 31d from the light source control unit 34 becomes relatively small at the time of foreground observation when the distal end portion 2c is brought closer to the object within the subject to perform observation, and the current value of the current to be supplied to the amber LED 31d from the light source control unit 34 becomes relatively large at the time of background observation when the distal end portion 2c is moved away from the object within the subject to perform observation, for example.

The control unit 44 performs an operation for reading table data TD from the memory 44a when detecting that the instruction to set the observation mode of the endoscope apparatus 1 to the special light observation mode has been issued. The control unit 44 detects a present current value CI of a current being supplied to the amber LED 31d in the light emitting unit 31 from the light source control unit 34 when detecting that the instruction to set the observation mode of the endoscope apparatus 1 to the special light observation mode has been issued.

Figures 4, 5:
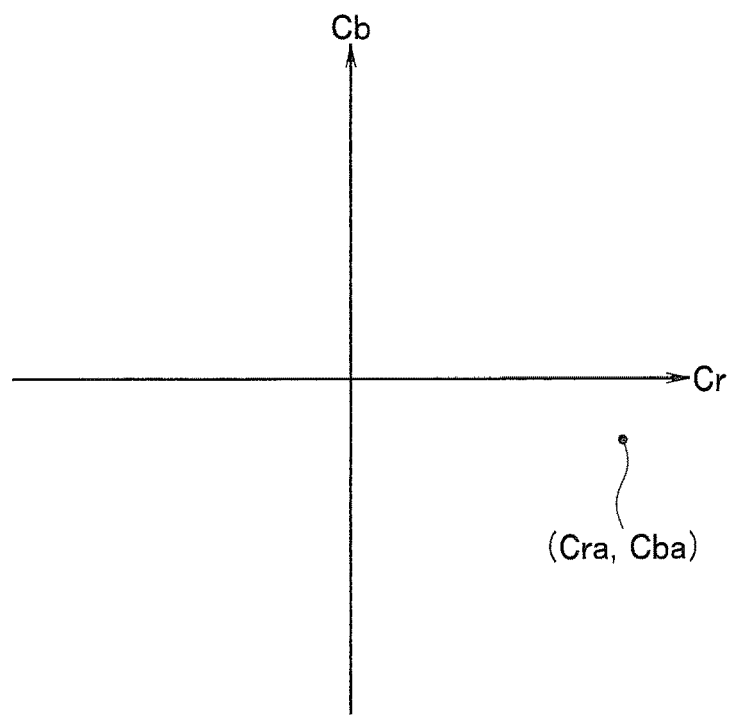
FIG. 4 is a diagram illustrating an example of table data used in processing of a processor according to the embodiment.
FIG. 5 is a diagram illustrating a reference color difference used in the processing of the processor according to the embodiment as a coordinate value in an orthogonal coordinate system.

The table data TD is generated as data representing a correspondence between a current value CV of a current to be supplied to the amber LED 31d and a signal output ratio SR of the image pickup signal to be outputted from the image pickup device 21b, as illustrated in FIG. 4, for example. FIG. 4 is a diagram illustrating an example of table data used in the processing of the processor according to the embodiment.

The current value CV is set as a value adapted to an operation mode of a light-adjusting operation for the amber LED 31d by the light source control unit 34. More specifically, if the light-adjusting operation for the amber LED 31d by the light source control unit 34 is performed with one ampere increments in a range from 1 amp to 10 amps, for example, ten current values included in the range are set as current values CVA, CVB, CVC, CVM included in the table data TD illustrated in FIG. 4. In the table data TD illustrated in FIG. 4, the current value CVA corresponds to a lower-limit value of the current to be supplied to the amber LED 31d, and the current value CVM corresponds to an upper-limit value of the current to be supplied to the amber LED 31d.

The signal output ratio SR is set as a value obtained by generating A light having a predetermined light amount LMT from the amber LED 31d, irradiating the A light onto a reference object including a region containing hemoglobin (or a region having a similar light absorption characteristic to the light absorption characteristic of hemoglobin) while gradually changing a center wavelength of the A light from 600 nm toward a shorter wavelength, acquiring a signal intensity SVI of an image pickup signal to be sequentially outputted from the image pickup device 21b in response to the irradiation with the A light, and calculating a ratio of the acquired signal intensity SVI to a reference signal intensity SVT (described below), for example. In other words, the signal intensity SVI is acquired as a signal intensity of an image pickup signal to be outputted from the image pickup unit 21 when A light having an intensity within a predetermined wavelength range in which a light absorption coefficient in the light absorption characteristic of hemoglobin sharply changes and having a center wavelength different from 600 nm is irradiated onto the object including the region containing hemoglobin.

In the present embodiment, the table data TD is generated on the premise that a relationship between the current value of the current to be supplied to the amber LED 31d in response to the light-adjusting operation of the light source control unit 34 and the center wavelength of the A light to be emitted from the amber LED 31*d* in response to the light-adjusting operation is known. The reference signal intensity SVT is a value obtained as a signal intensity of an image pickup signal to be outputted from the image pickup device 21*b* when the A light having the predetermined light amount LMT and having the center wavelength set to 600 nm is irradiated onto the above-described reference object.

Therefore, in the table data TD illustrated in FIG. 4, the signal output ratio SR corresponding to the current value CVM corresponding to the upper-limit value in the light-adjusting operation of the light source control unit 34 and set such that the center wavelength of the A light to be emitted from the amber LED 31*d* is 600 nm is set to 1.0. In the table data TD illustrated in FIG. 4, a correspondence between the current values CVA, CVB, CVC, . . . belonging to a range of the light-adjusting operation by the light source control unit 34 and set such that the center wavelength of the A light to be emitted from the amber LED 31*d* is less than 600 nm and signal output ratios SRA, SRB, SRC, . . . each acquired as a value that is more than 0 and less than 1.0 is illustrated.

Note that according to the present embodiment, data representing a correspondence between a temperature TV of the amber LED 31*d* and the signal output ratio SR of the image pickup signal to be outputted from the image pickup device 21*b*, for example, may be stored as the table data TD in the memory 44*a* instead of the above-described data. In such a case, the control unit 44 may detect a current temperature CT of the amber LED 31*d*, specify a temperature TV corresponding to the detected current temperature CT based on the table data TD, acquire a signal output ratio SR associated with the specified temperature TV, and output a control signal including the acquired signal output ratio SR to each of the color adjustment processing unit 42*a* and the color correction processing unit 42*b*. According to the present embodiment, a spectroscopic detector capable of detecting a current center wavelength WP of the A light to be emitted from the amber LED 31*d* may be provided in the light source apparatus 3, and a signal output ratio SR corresponding to a detection result of the spectroscopic detector may be acquired by the control unit 44, for example. According to the present embodiment, a plurality of table data TD generated for each individual identification number of the amber LED 31*d* may be stored in the memory 44*a*, for example.

The control unit 44 refers to the table data TD read from the memory 44*a*, to specify a current value CV corresponding to the present current value CI of the current being supplied to the amber LED 31*d* in the light emitting unit 31 from the light source control unit 34, acquires a signal output ratio SR associated with the specified current value CV, and outputs a control signal including the acquired signal output ratio SR to each of the color adjustment processing unit 42*a* and the color correction processing unit 42*b*.

In other words, the control unit 44 in the present embodiment refers to the table data TD based on a detection result obtained by detecting a present current value CI corresponding to a parameter representing a current operation state of the amber LED 31*d* as a generation source of the A light in the light emitting unit 31, to acquire signal intensity information as information about the signal intensity of the image pickup signal to be outputted from the image pickup unit 21 in response to the irradiation of the object including the region containing hemoglobin with the A light. The control unit 44 in the present embodiment acquires as signal intensity information the signal output ratio SR to be calculated as the ratio of the signal intensity SVI to the reference signal intensity SVT. The control unit 44 in the present embodiment performs an operation for outputting the control signal including the signal output ratio SR to each of the color adjustment processing unit 42*a* and the color correction processing unit 42*b* as an operation corresponding to control to maintain a ratio of respective brightnesses of the image data used for generating the observation image by the observation image generation unit 43 to be a predetermined ratio based on the signal intensity information. Note that the control unit 44 in the present embodiment may detect the current temperature CT of the amber LED 31*d* as the parameter representing the current operation state of the amber LED 31*d* to obtain a detection result. The control unit 44 in the present embodiment may detect the current center wavelength WP of the A light from the amber LED 31*d* as the parameter representing the current operation state of the amber LED 31*d* to obtain a detection result. The control unit 44 in the present embodiment may acquire signal intensity information (a signal output ratio SR) corresponding to the individual identification number of the amber LED 31*d*.

The color adjustment processing unit 42*a* subjects the image data PG and PR to be outputted from the signal processing unit 41 to color adjustment processing in the special light observation mode in response to the control signal to be outputted from the control unit 44. More specifically, the color adjustment processing unit 42*a* performs as color adjustment processing processing for multiplying the pixel value of each of the pixels in the image data PG by the signal output ratio SR included in the control signal to be outputted from the control unit 44 and processing for multiplying the pixel value of each of the pixels in the image data PR by the signal output ratio SR. In other words, according to the color adjustment processing, image data SPG obtained by multiplying the pixel value of each of the pixels in the image data PG by the signal output ratio SR and image data SPR obtained by multiplying the image data PR by the signal output ratio SR are outputted from the color adjustment processing unit 42*a* to the color correction processing unit 42*b*.

Note that according to the present embodiment, processing for multiplying the pixel value of each of the pixels in the image data PA by the reciprocal of the signal output ratio SR, for example, may be performed in the color adjustment processing unit 42*a*. If the processing has been performed in the color adjustment processing unit 42*a*, the image data PG, image data IPA obtained by multiplying the pixel value of each of the pixels in the image data PA by the reciprocal of the signal output ratio SR, and the image data PR are outputted to the color correction processing unit 42*b*.

According to the present embodiment, the color adjustment processing unit 42*a* may perform as color adjustment processing either one of processing for obtaining the image data SPG and SPR and processing for obtaining the image data IPA. In other words, the color adjustment processing unit 42*a* in the present embodiment may perform as color adjustment processing either one of processing for adjusting the brightness of the image data PA and processing for adjusting the respective brightnesses of the image data PG and PR based on the signal output ratio SR obtained in response to the control by the control unit 44.

The color correction processing unit 42*b* performs processing for calculating color differences Cr and Cb for each of the pixels based on the image data SPG, PA, and SPR to be outputted from the color adjustment processing unit 42*a*. The color correction processing unit 42*b* performs processing for acquiring the signal output ratio SR included in the control signal to be outputted from the control unit 44.

Note that respective values of the color differences Cr and Cb to be calculated by the color correction processing unit 42b in the present embodiment can be obtained by applying the pixel value of the image data SPG to a B (blue) component in a known conversion equation, applying a pixel value of the image data PA to a G (green) component in the conversion equation, and applying a pixel value of the image data SPR to an R (red) component in the conversion equation.

The color correction processing unit 42b extracts a region of interest AP corresponding to a pixel group in which both the color differences Cr and Cb respectively take negative values in the image data having each of the color components to be outputted from the color adjustment processing unit 42a. The color correction processing unit 42b performs processing using the following numerical equation (1), to set a color correction coefficient Tp corresponding to the color differences Cr and Cb calculated as described above for each of pixels included in the region of interest AP in each of the image data SPG and SPR. Note that in the following numerical equation (1), Fa and Fb respectively represent predetermined constants, Cra and Cba respectively represent values of reference color differences set depending on a reference color of a living body, and Crt and Cbt respectively represent values of color differences calculated in a pixel of interest included in the region of interest AP. In the following numerical equation (1), |Crt−Cra| represents an absolute value of a value obtained by subtracting the reference color difference Cra from the color difference Crt, and |Cbt−Cba| represents an absolute value of a value obtained by subtracting the reference color difference Cba from the color difference Cbt.

$$Tp=(1+Fa\times|Crt-Cra|)\times(1+Fb\times|Cbt-Cba|) \quad (1)$$

In other words, the color correction coefficient Tp is set as a value that monotonously increases as a color of the pixel of interest included in the region of interest AP in each of the image data SPG and SPR moves away from the reference color of the living body.

Note that according to the present embodiment, the reference color differences Cra and Cba may be respectively set as values to be plotted as coordinate values in a fourth quadrant in a CrCb coordinate system as an orthogonal coordinate system using the color difference Cr as a horizontal axis and using the color difference Cb as a vertical axis, for example (see FIG. 5). In other words, according to the present embodiment, the value of the reference color difference Cra may be set to be larger than 0, and the value of the reference color difference Cba may be set to be smaller than 0. FIG. 5 is a diagram illustrating a reference color difference used in the processing of the processor according to the embodiment as a coordinate value in the orthogonal coordinate system.

According to the present embodiment, when data representing a correspondence between the current value CV and the respective values of the reference color differences Cra and Cba is included in the table data TD, for example, the control unit 44 may perform control to change the respective values of the reference color differences Cra and Cba depending on a detection result of the present current value CI being supplied to the amber LED 31d, for example.

The color correction processing unit 42b performs calculation by applying the signal output ratio SR and the color correction coefficient Tp to the following numerical equation (2), to correct the respective pixel values of the pixels included in the region of interest AP in the image data SPG and the respective pixel values of the pixels included in the region of interest AP in the image data SPR. Note that in the following numerical equation (2), Pa represents a pixel value before correction of the pixel of interest included in the region of interest AP in each of the image data SPG and SPR, and Pb represents a pixel value after correction of the pixel of interest.

$$Pb=Pa\times[1-Tp+(Tp/SR)] \quad (2)$$

In other words, according to the foregoing numerical equation (2), color correction processing for suppressing a saturation of a region containing no hemoglobin in each of the image data SPG and SPR is performed in the color correction processing unit 42b based on the signal output ratio SR to be obtained in response to the control by the control unit 44 and the color differences Cr and Cb calculated using the image data SPG, PA, and SPR obtained as a processing result of the color adjustment processing by the color adjustment processing unit 42a. If the processing using the foregoing numerical equation (2) has been performed in the color correction processing unit 42b, image data SCPG obtained by subjecting each of the pixels included in the region of interest AP in the image data SPG to the color correction processing, the image data PA, and image data SCPR obtained by subjecting each of the pixels included in the region of interest AP in the image data SPR to the color correction processing are outputted from the color correction processing unit 42b to the observation image generation unit 43.

The color correction processing unit 42b in the present embodiment may perform processing for correcting a pixel value of each of pixels included in a region of interest AP in the image data PA using the following numerical equation (3), for example. Note that in the following numerical equation (3), Pc represents a pixel value before correction of a pixel of interest included in the region of interest AP in the image data PA, and Pd represents a pixel value after correction of the pixel of interest.

$$Pd=Pc\times(1-Tp+SR\times Tp) \quad (3)$$

In other words, according to the foregoing numerical equation (3), color correction processing for suppressing a saturation of a region containing no hemoglobin in the image data PA is performed in the color correction processing unit 42b based on the signal output ratio SR obtained in response to the control by the control unit 44 and the color differences Cr and Cb calculated using the image data SPG, PA, and SPR obtained as a processing result of the color adjustment processing by the color adjustment processing unit 42a. When processing using the foregoing numerical equation (3) has been performed in the color correction processing unit 42b, the image data SPG, image data CPA obtained by subjecting each of the pixels included in the region of interest AP in the image data PA to the color correction processing, and the image data SPR are outputted to the observation image generation unit 43.

According to the present embodiment, the color correction processing unit 42b may perform as color correction processing either one of the processing using the foregoing numerical equation (2) and the processing using the foregoing numerical equation (3).

The observation image generation unit 43 generates a special light observation image by assigning the image data SCPG to be outputted via the color correction processing unit 42b to the B channel of the display apparatus 5, assigning the image data PA to be outputted via the color correction processing unit 42b to the G channel of the display apparatus 5, and assigning the image data SCPR to be outputted via the color correction processing unit 42b to the R channel of the display apparatus 5 and outputs the generated special light observation image to the display apparatus 5, for example, in the special light observation mode in response to the control signal to be outputted from the control unit 44.

In a wavelength band in the vicinity of 600 nm as the original center wavelength of the A light to be emitted from the amber LED 31d, the light absorption coefficient of hemoglobin sharply increases as a wavelength of the illumination light shifts toward a shorter wavelength. The center wavelength of the A light to be emitted from the amber LED 31d shifts toward a wavelength of less than 600 nm as the current value of the current to be supplied to the amber LED 31d from the light source control unit 34 decreases, for example.

Accordingly, when the light-adjusting operation to bring the ratio of the current brightness SCB to the brightness target value STB closer to 1 has been merely performed, for example, the wavelength band of the A light shifts toward the shorter wavelength from the original wavelength band as the current value of the current to be supplied to the amber LED 31d decreases so that a light amount of return light of the A light, an image of which is picked up by the image pickup device 21b, decreases as an absorption amount of the A light in a region containing hemoglobin such as a blood vessel and blood increases at the time of foreground observation. In other words, when the above-described light-adjusting operation has been merely performed in the special light observation mode, there can occur a phenomenon that a color tone of the region containing hemoglobin in the observation image to be displayed on the display apparatus 5 greatly differs between the time of foreground observation and the time of background observation.

On the other hand, according to the present embodiment, either one of processing for acquiring the signal output ratio SR corresponding to the detection result of the present current value CI being supplied to the amber LED 31d by referring to the table data TD and reducing the respective brightnesses of the image data PG and PR depending on the acquired signal output ratio SR and processing for increasing the brightness of the image data PA depending on the acquired signal output ratio SR is performed. Further, according to the present embodiment, each of the pixels included in the above-described region of interest AP is subjected to either one of the processing using the foregoing numerical equation (2) and the processing using the foregoing numerical equation (3).

Therefore, according to the present embodiment, even when a light-adjusting operation corresponding to an observation distance from the object has been performed in the special light observation mode, the color tone of the region containing hemoglobin such as a blood vessel and blood in the observation image to be displayed on the display apparatus 5 can be maintained to be a constant color tone. According to the present embodiment, even when the light-adjusting operation corresponding to the observation distance from the object has been performed in the special light observation mode, a color tone of a region containing no hemoglobin such as a connective tissue and a treatment instrument in the observation image to be displayed on the display apparatus 5 can be maintained to be a constant color tone. Therefore, according to the present embodiment, a burden on a user who performs treatment for a desired site within a living body while observing a deep blood vessel existing at a depth of a living tissue in the desired site can be reduced, for example.

Note that according to the present embodiment, an image pickup device 21b having an image pickup surface provided with a primary color filter or a complementary color filter may pick up an image of an object to obtain image data respectively having color components, for example. In such a case, when the observation mode of the endoscope apparatus 1 is set to the special light observation mode, for example, control to cause the amber LED 31d to emit light and control to cause the green LED 31c and the red LED 31e to simultaneously emit lights may be repeatedly performed in this order.

According to the present embodiment, an image pickup device 21b having an image pickup surface provided with a color filter including a filter configured to transmit only a wavelength band of G light, a filter configured to transmit only a wavelength band of A light, and a filter configured to transmit only a wavelength band of R light may pick up an image of an object to obtain image data respectively having color components, for example. In such a case, when the observation mode of the endoscope apparatus 1 is set to the special light observation mode, control to cause the green LED 31c, the amber LED 31d, and the red LED 31e to simultaneously emit lights while causing the violet LED 31a and the blue LED 31b to quench lights may be performed, for example.

According to the present embodiment, the B light may be irradiated onto the object instead of the G light in the special light observation mode, for example. In such a case, when the observation mode of the endoscope apparatus 1 is set to the special light observation mode, the image data PB is acquired instead of the image data PG, and the color adjustment processing by the color adjustment processing unit 42a and the color correction processing by the color correction processing unit 42b are sequentially performed for the image data PB, for example.

According to the present embodiment, a light source configured to generate IR light as near-infrared narrow band light having a center wavelength set to the vicinity of 800 nm may be provided in the light source apparatus 3, and a configuration for separating return light of the IR light from return light of light other than the IR light and picking up an image of the separated return light may be provided in the image pickup unit 21, for example. In such a case, when the observation mode of the endoscope apparatus 1 is set to the special light observation mode, the IR light is irradiated onto an object instead of the R light, image data PIR as image data having a near-infrared component obtained by performing image pickup of return light from the object irradiated with the IR light is acquired, and the color adjustment processing by the color adjustment processing unit 42a and the color correction processing by the color correction processing unit 42b are sequentially performed for the image data PIR. Note that the above-described IR light may have an intensity on the side of a longer wavelength than the wavelength of the A light (and the R light), and may have an intensity outside the predetermined wavelength range in which the light absorption coefficient in the light absorption characteristic of hemoglobin sharply changes, for example.

According to the present embodiment, the control unit 44 may perform control to adjust an exposure time period when picking up an image of return light of the A light in the image pickup device 21b based on the signal output ratio SR instead of the color adjustment processing unit 42a performing the color adjustment processing based on the signal output ratio SR in the special light observation mode, for example. More specifically, the control unit 44 may subject the image pickup device 21b to control to set an exposure time period when picking up an image of return light of the G light and an exposure time period when picking up an image of return light of the R light to ETP, and set an exposure time period ETQ when picking up an image of return light of the A light to (1/SR) times of the exposure time period ETP in the special light observation mode, for example Note that in such a case, control to set a light emission time period of the amber LED 31*d* to the exposure time period ETQ or more may be together performed.

According to the present embodiment, the control unit 44 may perform control to adjust a gain of an image pickup signal obtained by performing image pickup of the return light of the A light in the image pickup device 21*b* based on the signal output ratio SR instead of the color adjustment processing unit 42*a* performing the color adjustment processing based on the signal output ratio SR in the special light observation mode, for example. More specifically, the control unit 44 may subject the image pickup device 21*b* to control to set a gain of an image pickup signal obtained by performing image pickup of the return light of the G light and a gain of an image pickup signal obtained by performing image pickup of the return light of the R light to GP, and set a gain GQ of an image pickup signal obtained by performing image pickup of the return light of the A light to (1/SR) times of the gain GP in the special light observation mode, for example.

According to the present embodiment, the control unit 44 may perform control to adjust the light amount of the A light to be emitted from the light emitting unit 31 based on the signal output ratio SR instead of the color adjustment processing unit 42*a* performing the color adjustment processing based on the signal output ratio SR in the special light observation mode, for example. More specifically, the control unit 44 may subject the light source control unit 34 to control to set the light amount of the G light and the light amount of the R light to be emitted from the light emitting unit 31 to LMP, and set a light amount LMQ of the A light to be emitted from the light emitting unit 31 to (1/SR) times of the light amount LMP in the special light observation mode, for example. Note that in such a case, either one of the light emission time period of the amber LED 31*d* and the current value of the current to be supplied to the amber LED 31*d* from the light source control unit 34 may be changed. Note that when the current value of the current to be supplied to the amber LED 31*d* from the light source control unit 34 is changed to set the light amount of the A light to (1/SR) times of the light amount of the G light and the R light, the point that the current value and the signal output ratio SR change in conjunction with each other, as indicated by the following numerical equation (4), for example, needs to be considered. Note that the following numerical equation (4) represents an example of a case where the current value of the current to be supplied to the amber LED 31*d* is changed from the present current value Ic (corresponding to the above-described current value CI) to a new current value In. In the following numerical equation (4), SRIc represents a signal output ratio corresponding to the current value Ic in the table data TD, and SRIn represents a signal output ratio corresponding to the current value In in the table data TD.

$$1/SRIc=(In \times SRIn)/(Ic \times SRIc) \quad (4)$$

When the numerical equation (4) is transformed, the following numerical equation (5) can be obtained.

$$0 = In \times SRIn - Ic \quad (5)$$

Assuming that the signal output ratio SR in the table data TD is approximated by a linear function of the current value CV, for example, the foregoing numerical equation (5) can be represented as a quadratic equation of the current value In. When control to supply a current having a current value In (>0) obtained as a solution of the above-described quadratic equation to the amber LED 31*d* is performed in the special light observation mode, a ratio of the current brightness SCB to the brightness target value STB can be brought closer to 1 while the light amount of the A light is set to (1/SR) times of the light amount of the G light and the R light.

In the present embodiment, color adjustment processing in a modification, described below, for example, may be performed in the color adjustment processing unit 42*a* instead of the above-described color adjustment processing in the special light observation mode. Note that a specific description of a portion to which the processing or the like, already described, is applicable will be appropriately omitted below for simplicity.

The color adjustment processing unit 42*a* performs processing for calculating each of color differences Cr and Cb based on image data PG, PA, and PR to be outputted from a signal processing unit 41. The color adjustment processing unit 42*a* performs processing for acquiring a signal output ratio SR included in a control signal to be outputted from the control unit 44.

Note that respective values of the color differences Cr and Cb to be calculated by the color adjustment processing unit 42*a* in the present modification can be obtained by applying a pixel value of the image data PG to a B component in a known conversion equation, applying a pixel value of the image data PA to a G component in the conversion equation, and applying a pixel value of the image data PR to an R component in the conversion equation.

The color adjustment processing unit 42*a* performs processing for setting a color adjustment coefficient Tq corresponding to the color differences Cr and Cb calculated as described above for each of pixels included in each of the image data PG and PR.

Note that the color adjustment coefficient Tq corresponds to the reciprocal of a color correction coefficient Tp obtained by applying the value of the color difference Cr calculated in a pixel of interest included in each of the image data PG and PR to Crt in the foregoing numerical equation (1) and applying the value of the color difference Cb calculated in the pixel of interest to Cbt in the foregoing numerical equation (1). Accordingly, the color adjustment coefficient Tq is set as a value that monotonously increases as a color of the pixel of interest included in each of the image data PG and PR comes closer to a reference color of a living body.

The color adjustment processing unit 42*a* performs calculation by applying the signal output ratio SR and the color adjustment coefficient Tq to the following numerical equation (6), to adjust each of a pixel value of each of the pixels included in the image data PG and a pixel value of each of the pixels included in the image data PR. Note that in the following numerical equation (6), Pc represents a pixel value before adjustment of the pixel of interest included in each of the image data PG and PR, and Pd represents a pixel value after adjustment of the pixel of interest.

$$Pd = Pc \times (1 - Tq + SR \times Tq) \quad (6)$$

In other words, according to the foregoing numerical equation (6), color adjustment processing for suppressing respective saturations of regions containing no hemoglobin in the image data PG and PR while adjusting respective brightnesses of the image data PG and PR based on the signal output ratio SR to be obtained in response to control by the control unit 44 and the color differences Cr and Cb calculated using the image data respectively having the color components to be outputted from the signal processing unit 41 is performed in the color adjustment processing unit 42a. If the processing using the foregoing numerical equation (6) has been performed in the color adjustment processing unit 42a, image data DPG obtained by subjecting each of the pixels included in the image data PG to the color adjustment processing and image data DPR obtained by subjecting each of the pixels included in the image data PR to the color adjustment processing can be obtained.

Note that when color adjustment processing using the foregoing numerical equation (6) is performed, the color correction processing by the color correction processing unit 42b is not required. Accordingly, if the color adjustment processing using the foregoing numerical equation (6) is performed, the image data DPG, the image data PA, and the image data DPR are outputted from the color correction processing unit 42b to the observation image generation unit 43. If the color adjustment processing using the foregoing numerical equation (6) is performed, the observation image generation unit 43 generates a special light observation image by assigning the image data DPG to be outputted via the image processing unit 42 to a B channel of the display apparatus 5, assigning the image data PA to be outputted via the image processing unit 42 to a G channel of the display apparatus 5, and assigning the image data DPR to be outputted via the image processing unit 42 to an R channel of the display apparatus 5, and outputs the generated special light observation image to the display apparatus 5.

The color adjustment processing unit 42a in the present modification may perform processing for adjusting the pixel value of each of the pixels included in the image data PA using the following numerical equation (7), for example. Note that in the following numerical equation (7), Pe represents a pixel value before adjustment of a pixel of interest included in the image data PA, and Pf represents a pixel value after adjustment of the pixel of interest.

$$Pf=Pe\times[1-Tq+(Tq/SR)] \quad (7)$$

In other words, according to the foregoing numerical equation (7), color adjustment processing for suppressing a saturation of a region containing no hemoglobin in the image data PA while adjusting a brightness of the image data PA is performed in the color adjustment processing unit 42a based on the signal output ratio SR to be obtained in response to the control by the control unit 44 and the color differences Cr and Cb calculated using the image data respectively having the color components to be outputted from the signal processing unit 41. If processing using the foregoing numerical equation (7) has been performed in the color adjustment processing unit 42a, image data DPA can be obtained by subjecting each of the pixels included in the image data PA to the color adjustment processing.

Note that when color adjustment processing using the foregoing numerical equation (7) is performed, the color correction processing by the color correction processing unit 42b is not required. Accordingly, if the color adjustment processing using the foregoing numerical equation (7) is performed, the image data PG, the image data DPA, and the image data PR are outputted from the color correction processing unit 42b to the observation image generation unit 43. If the color adjustment processing using the foregoing numerical equation (7) is performed, the observation image generation unit 43 generates a special light observation image by assigning the image data PG to be outputted via the image processing unit 42 to the B channel of the display apparatus 5, assigning the image data DPA to be outputted via the image processing unit 42 to the G channel of the display apparatus 5, and assigning the image data PR to be outputted via the image processing unit 42 to the R channel of the display apparatus 5 and outputs the generated special light observation image to the display apparatus 5.

According to the present modification, the color adjustment processing unit 42a may perform as color adjustment processing either one of the processing using the foregoing numerical equation (6) and the processing using the foregoing numerical equation (7).

On the other hand, according to the present embodiment, processing for maintaining a color tone of an observation image to be displayed when observing a capillary existing in a surface layer of a living tissue, for example, may be performed by appropriately deforming an operation of each of the units when the observation mode of the endoscope apparatus 1 is set to the special light observation mode. A specific example of an operation, processing, and the like according to such a modification will be described below. Note that a case where a wavelength band of V light to be emitted from the violet LED 31a shifts toward a shorter wavelength from an original wavelength band will be described below as an example.

The control unit 44 generates a control signal for sequentially emitting the V light and the G light from the light source apparatus 3 and outputs the generated control signal to the light source control unit 34 when detecting that an instruction to set the observation mode of the endoscope apparatus 1 to the special light observation mode has been issued.

The light source control unit 34 subjects the light emitting unit 31 to control to cause the violet LED 31a and the green LED 31c to alternately and repeatedly emit lights while causing the blue LED 31b, the amber LED 31d, and the red LED 31e to quench lights, for example, in the special light observation mode in response to the control signal to be outputted from the control unit 44. The V light and the G light are sequentially irradiated as illumination light onto the object, and an image pickup signal generated by performing image pickup of return light of the illumination light is sequentially outputted to the signal processing unit 41 from the image pickup device 21b in response to such an operation of the light source control unit 34. In other words, the image pickup unit 21 in the present modification picks up an image of return light from an object including a region containing hemoglobin illuminated with the V light and the G light and outputs an image pickup signal in the special light observation mode.

The signal processing unit 41 subjects the image pickup signal to be sequentially outputted from the image pickup device 21b to predetermined signal processing, to generate image data PV as image data having a violet component obtained by performing image pickup of return light from the object irradiated with the V light and the image data PG and output the generated image data to each of the image processing unit 42 and the control unit 44.

The control unit 44 performs brightness detection processing for detecting a current brightness SCL in the special light observation mode based on the image data respectively having the color components to be outputted from the signal processing unit 41.

More specifically, the control unit 44 performs processing for calculating an average value of respective pixel values of pixels included in each of the image data PV and PG to be outputted from the signal processing unit 41, and detecting the calculated average value as the current brightness SCL in the special light observation mode, for example, as the above-described brightness detection processing. Note that the control unit 44 may perform processing for detecting either one of a weighted average value of the respective pixel values of the pixels included in each of the image data PV and PG to be outputted from the signal processing unit 41 and the average value of the respective pixel values of the pixels included in the image data PV to be outputted from the signal processing unit 41 as the current brightness SCL in the special light observation mode, for example, as the above-described brightness detection processing. The control unit 44 may use an entire area of the image data to be outputted from the signal processing unit 41 as a processing target or may use only a partial region of the image data to be outputted from the signal processing unit 41 as a processing target when performing the above-described brightness detection processing.

The control unit 44 generates a control signal for performing a light-adjusting operation to bring the current brightness SCL obtained as a processing result of the above-described brightness detection processing closer to a brightness target value STL in the special light observation mode and outputs the generated control signal to the light source control unit 34. More specifically, the control unit 44 generates a control signal for performing a light-adjusting operation to bring a ratio of the current brightness SCL to the brightness target value STL (SCL/STL) closer to 1 and outputs the generated control signal to the light source control unit 34, for example. In other words, according to such a light-adjusting operation, a current value of a current to be supplied to the violet LED 31a from the light source control unit 34 becomes relatively small at the time of foreground observation when the distal end portion 2c is brought closer to the object within the subject to perform observation, and the current value of the current to be supplied to the violet LED 31a from the light source control unit 34 becomes relatively large at the time of background observation when the distal end portion 2c is moved away from the object within the subject to perform observation, for example.

The control unit 44 performs an operation for reading table data TE from the memory 44a when detecting that an instruction to set the observation mode of the endoscope apparatus 1 to the special light observation mode has been issued. The control unit 44 detects a present current value CJ of a current being supplied to the violet LED 31a in the light emitting unit 31 from the light source control unit 34 when detecting that an instruction to set the observation mode of the endoscope apparatus 1 to the special light observation mode has been issued.

Figures 6, 7:
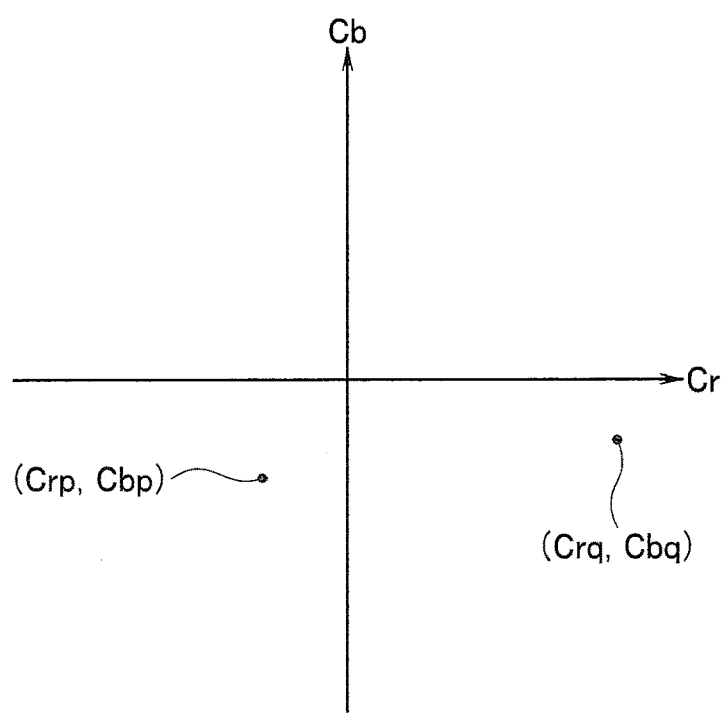
FIG. 6 is a diagram illustrating an example of table data used in the processing of the processor according to the embodiment.
FIG. 7 is a diagram illustrating reference color differences used in the processing of the processor according to the embodiment as a coordinate value in an orthogonal coordinate system.

The table data TE is generated as data representing a correspondence between a current value CW of a current to be supplied to the violet LED 31a and a signal output ratio SS of the image pickup signal to be outputted from the image pickup device 21b, as illustrated in FIG. 6, for example. FIG. 6 is a diagram illustrating an example of table data used in the processing of the processor according to the embodiment.

The current value CW is set as a value to be adapted to an operation mode of a light-adjusting operation for the violet LED 31a by the light source control unit 34. More specifically, if the light-adjusting operation for the violet LED 31a by the light source control unit 34 is performed with 1 ampere increments in a range from 1 amp to 10 amps, for example, ten current values included in the range are set as current values CWA, CWB, CWC, CWM included in the table data TE illustrated in FIG. 6. In the table data TE illustrated in FIG. 6, the current value CWA corresponds to a lower-limit value of the current to be supplied to the violet LED 31a, and the current value CWM corresponds to an upper-limit value of the current to be supplied to the violet LED 31a.

The signal output ratio SS is set as a value obtained by generating V light having a predetermined light amount LMU from the violet LED 31a, irradiating the V light onto a reference object including a region containing hemoglobin (or a region having a similar light absorption characteristic to the light absorption characteristic of hemoglobin) while gradually changing a center wavelength of the V light from 410 nm toward a shorter wavelength (a wavelength different from 410 nm), acquiring a signal intensity SVJ of an image pickup signal to be sequentially outputted from the image pickup device 21b in response to the irradiation with the V light, and calculating a ratio of the acquired signal intensity SVJ to a reference signal intensity SVU (described below), for example. In other words, the signal intensity SVJ is acquired as a signal intensity of an image pickup signal to be outputted from the image pickup unit 21 when V light having an intensity within a predetermined wavelength range in which a light absorption coefficient in the light absorption characteristic of hemoglobin sharply changes and having a center wavelength different from 410 nm is irradiated onto the object including the region containing hemoglobin.

In the present embodiment, the table data TE is generated on the premise that a relationship between the current value of the current to be supplied to the violet LED 31a in response to the light-adjusting operation of the light source control unit 34 and the center wavelength of the V light to be emitted from the violet LED 31a in response to the light-adjusting operation is known. The reference signal intensity SVU is a value obtained as a signal intensity of an image pickup signal to be outputted from the image pickup device 21b when the V light having the predetermined light amount LMU and having the center wavelength set to 410 nm is irradiated onto the above-described reference object.

Therefore, in the table data TE illustrated in FIG. 6, the signal output ratio SS corresponding to the current value CWM corresponding to the upper-limit value in the light-adjusting operation of the light source control unit 34 and set such that the center wavelength of the V light to be emitted from the violet LED 31a is 410 nm is set to 1.0. In the table data TE illustrated in FIG. 6, a correspondence between the current values CWA, CWB, CWC, . . . belonging to a range of the light-adjusting operation by the light source control unit 34 and set such that the center wavelength of the V light to be emitted from the violet LED 31a is less than 410 nm and signal output ratio SSA, SSB, SSC, . . . each acquired as a value that is more than 1.0 is illustrated.

Note that according to the present modification, data representing a correspondence between a temperature TW of the violet LED 31a and the signal output ratio SS of the image pickup signal to be outputted from the image pickup device 21b, for example, may be stored as the table data TE in the memory 44a instead of the above-described data. In such a case, the control unit 44 may detect a current temperature CU of the violet LED 31a, specify a temperature TW corresponding to the detected current temperature CU based on the table data TE, acquire a signal output ratio SS associated with the specified temperature TW, and output a control signal including the acquired signal output ratio SS to each of the color adjustment processing unit 42a and the color correction processing unit 42b. According to the present modification, a spectroscopic detector capable of detecting a current center wavelength WQ of the V light emitted from the violet LED 31*a* may be provided in the light source apparatus 3, and a signal output ratio SS corresponding to a detection result of the spectroscopic detector may be acquired by the control unit 44, for example. According to the present modification, a plurality of table data TE generated for each individual identification number of the violet LED 31*a* may be stored in the memory 44*a*, for example.

The control unit 44 refers to the table data TE read from the memory 44*a*, to specify a current value CW corresponding to the present current value CJ of the current being supplied to the violet LED 31*a* in the light emitting unit 31 from the light source control unit 34, acquires a signal output ratio SS associated with the specified current value CW, and outputs a control signal including the acquired signal output ratio SS to each of the color adjustment processing unit 42*a* and the color correction processing unit 42*b*.

In other words, the control unit 44 in the present modification refers to the table data TE based on a detection result obtained by detecting a present current value CJ corresponding to a parameter representing a current operation state of the violet LED 31*a* as a generation source of the V light, to acquire signal intensity information as information about the signal intensity of the image pickup signal to be outputted from the image pickup unit 21 in response to the irradiation of the object including the region containing hemoglobin with the V light. The control unit 44 in the present modification acquires as signal intensity information the signal output ratio SS to be calculated as the ratio of the signal intensity SVJ to the reference signal intensity SVU. The control unit 44 in the present modification performs an operation for outputting a control signal including the signal output ratio SS to each of the color adjustment processing unit 42*a* and the color correction processing unit 42*b* as an operation corresponding to control to maintain a ratio of respective brightnesses of image data used for generating an observation image by the observation image generation unit 43 to be a predetermined ratio based on the signal intensity information. Note that the control unit 44 in the present modification may detect the current temperature CU of the violet LED 31*a* as the parameter representing the current operation state of the violet LED 31*a* to obtain a detection result. The control unit 44 in the present modification may detect the current center wavelength WQ of the V light from the violet LED 31*a* as the parameter representing the current operation state of the violet LED 31*a* to obtain a detection result. The control unit 44 in the present modification may acquire signal intensity information (a signal output ratio SS) corresponding to the individual identification number of the violet LED 31*a*.

The color adjustment processing unit 42*a* subjects the image data PG to be outputted from the signal processing unit 41 to color adjustment processing in the special light observation mode in response to the control signal to be outputted from the control unit 44. More specifically, the color adjustment processing unit 42*a* performs as color adjustment processing processing for multiplying the pixel value of each of the pixels in the image data PG by the signal output ratio SS included in the control signal to be outputted from the control unit 44. In other words, according to the color adjustment processing, the image data PV and image data TPG obtained by multiplying the pixel value of each of the pixels in the image data PG by the signal output ratio SS are outputted from the color adjustment processing unit 42*a* to the color correction processing unit 42*b*.

Note that according to the present modification, processing for multiplying the pixel value of each of the pixels in the image data PV by the reciprocal of the signal output ratio SS, for example, may be performed in the color adjustment processing unit 42*a*. If the processing has been performed in the color adjustment processing unit 42*a*, image data JPV obtained by multiplying the pixel value of each of the pixels in the image data PV by the reciprocal of the signal output ratio SS and the image data PG are outputted to the color correction processing unit 42*b*.

According to the present modification, the color adjustment processing unit 42*a* may perform as color adjustment processing either one of processing for obtaining the image data TPG and processing for obtaining the image data JPV. In other words, the color adjustment processing unit 42*a* in the present modification performs as color adjustment processing either one of processing for adjusting the brightness of the image data PV and processing for adjusting the brightness of the image data PG based on the signal output ratio SS obtained in response to the control by the control unit 44.

The color correction processing unit 42*b* performs processing for calculating color differences Cr and Cb for each of the pixels based on the image data PV and TPG to be outputted from the color adjustment processing unit 42*a*. The color correction processing unit 42*b* performs processing for acquiring the signal output ratio SS included in the control signal to be outputted from the control unit 44.

Note that respective values of the color differences Cr and Cb to be calculated by the color correction processing unit 42*b* in the present modification can be obtained by applying the pixel value of the image data PV to a B component and a G component in a known conversion equation and applying a pixel value of the image data TPG to an R component in the conversion equation.

The color correction processing unit 42*b* extracts a region of interest AQ corresponding to a pixel group in which both the color differences Cr and Cb respectively take positive values from the image data having each of the color components to be outputted from the color adjustment processing unit 42*a*. The color correction processing unit 42*b* performs processing using the following numerical equation (8), to perform processing for setting a color correction coefficient Tr corresponding to the color differences Cr and Cb calculated as described above for each of pixels included in the region of interest AQ in the image data TPG. Note that in the following numerical equation (8), Fp, Fq, Fr, and Fs respectively represent predetermined constants, Crp and Cbp respectively represent values of reference color differences set depending on a reference color of an intermediate-layer blood vessel existing in an intermediate layer of the living tissue, Crq and Cbq respectively represent values of reference color differences set depending on a reference color of the capillary existing in the surface layer of the living tissue, and Cm and Cbu respectively represent values of color differences calculated in a pixel of interest included in the region of interest AQ. In the following numerical equation (8), |Crx| represents an absolute value of a value obtained by subtracting the reference color difference Crp from the color difference Cm, |Cbx| represents an absolute value of a value obtained by subtracting the reference color difference Cbp from the color difference Cbu, |Cry| represents an absolute value of a value obtained by subtracting the reference color difference Crq from the color difference Cru, and |Cby| represents an absolute value of a value obtained by subtracting the reference color difference Cbq from the color difference Cbu.

$$Tr=[(1+Fp\times|Crx|)\times(1+Fq\times|Cbx|)\times(1+Fr\times|Cry|)\times(1+Fs\times|Cby|)]/\{[(1+Fp\times|Crx|)\times(1+Fq\times|Cbx|)]+[(1+Fr\times|Cry|)\times(1+Fs\times|Cby|)]\} \quad (8)$$

In other words, the color correction coefficient Tr is set as a value that monotonously increases as a color of the pixel of interest included in the region of interest AQ in the image data TPG moves away from both the reference color of the intermediate-layer blood vessel and the reference color of the capillary.

Note that according to the present modification, the reference color differences Crp and Cbp may be respectively set as values to be plotted as coordinate values in a third quadrant in a CrCb coordinate system, for example (see FIG. 7). In other words, according to the present modification, the value of the reference color difference Crp may be set to be smaller than 0, and the value of the reference color difference Cbp may be set to be smaller than 0. FIG. 7 is a diagram illustrating a reference color difference used in the processing of the processor according to the embodiment as a coordinate value in an orthogonal coordinate system.

According to the present modification, the reference color differences Crq and Cbq may be respectively set as values to be plotted as coordinate values in a fourth quadrant in the CrCb coordinate system, for example (see FIG. 7). In other words, according to the present modification, the value of the reference color difference Crq may be set to be larger than 0, and the value of the reference color difference Cbq may be set to be smaller than 0.

According to the present modification, when data representing a correspondence among the current value CW, the respective values of the reference color differences Crp and Cbp, and the respective values of the reference color differences Crq and Cbq is included in the table data TE, for example, the control unit 44 may perform control to change the respective values of the reference color differences Crp, Cbp, Crq, and Cbq depending on a detection result of the present current value CJ of the current being supplied to the violet LED 31a.

The color correction processing unit 42b performs calculation by applying the signal output ratio SS and the color correction coefficient Tr to the following numerical equation (9), to correct the respective pixel values of the pixels included in the region of interest AQ in the image data TPG. Note that in the following numerical equation (9), Pg represents a pixel value before correction of the pixel of interest included in the region of interest AQ in the image data TPG, and Ph represents a pixel value after correction of the pixel of interest.

$$Ph=Pg\times[1-Tr+(Tr/SS)] \quad (9)$$

In other words, according to the foregoing numerical equation (9), color correction processing for suppressing a saturation of a region containing no hemoglobin in the image data TPG is performed in the color correction processing unit 42b based on the signal output ratio SS to be obtained in response to the control by the control unit 44 and the color differences Cr and Cb calculated using the image data PV and TPG obtained as a processing result of color adjustment processing by the color adjustment processing unit 42a. If the processing using the foregoing numerical equation (9) has been performed in the color correction processing unit 42b, the image data PV and image data TCPG obtained by subjecting each of the pixels included in the region of interest AQ in the image data TPG to color correction processing are outputted from the color correction processing unit 42b to the observation image generation unit 43.

The color correction processing unit 42b may perform processing for correcting a pixel value of each of pixels included in a region of interest AQ in the image data PV using the following numerical equation (10), for example. Note that in the following numerical equation (10), Pi represents a pixel value before correction of the pixel of interest included in the region of interest AQ in the image data PV, and Pj represents a pixel value after correction of the pixel of interest.

$$Pj=Pi\times(1-Tr+SS\times Tr) \quad (10)$$

In other words, according to the foregoing numerical equation (10), color correction processing for suppressing a saturation of a region containing no hemoglobin in the image data PV is performed in the color correction processing unit 42b based on the signal output ratio SS obtained in response to the control by the control unit 44 and the color differences Cr and Cb calculated using the image data PV and TPG obtained as a processing result of the color adjustment processing by the color adjustment processing unit 42a. When processing using the foregoing numerical equation (10) has been performed in the color correction processing unit 42b, image data EPV obtained by subjecting each of the pixels included in the region of interest AQ in the image data PV to the color correction processing and the image data TPG are outputted to the observation image generation unit 43.

According to the present modification, the color correction processing unit 42b may perform as color correction processing either one of the processing using the foregoing numerical equation (9) and the processing using the foregoing numerical equation (10).

The observation image generation unit 43 generates a special light observation image by assigning the image data PV to be outputted via the color correction processing unit 42b to the B channel and the G channel of the display apparatus 5 and assigning the image data TCPG to be outputted via the color correction processing unit 42b to the R channel of the display apparatus 5 and outputs the generated special light observation image to the display apparatus 5, for example, in the special light observation mode in response to the control signal to be outputted from the control unit 44.

In a wavelength band in the vicinity of 410 nm as the original center wavelength of the V light to be emitted from the violet LED 31a, the light absorption coefficient of hemoglobin sharply decreases as a wavelength of illumination light shifts toward a shorter wavelength. The center wavelength of the V light to be emitted from the violet LED 31a shifts toward a wavelength of less than 410 nm as the current value of the current to be supplied to the violet LED 31a from the light source control unit 34 decreases, for example.

Accordingly, when the light-adjusting operation to bring the ratio of the current brightness SCL to the brightness target value STL closer to 1 has been merely performed, for example, the wavelength band of the V light shifts toward the shorter wavelength from the original wavelength band as the current value of the current to be supplied to the violet LED 31a decreases so that a light amount of return light of the V light, an image of which is picked up by the image pickup device 21b, increases as an absorption amount of the V light in a region containing hemoglobin such as a blood vessel and blood decreases at the time of foreground observation. In other words, when the above-described light-adjusting operation has been merely performed in the special light observation mode, there can occur a phenomenon that a color tone of the region containing hemoglobin in the observation image to be displayed on the display apparatus 5 greatly differs between the time of foreground observation and the time of background observation.

On the other hand, according to the present modification, either one of processing for acquiring the signal output ratio SS corresponding to the detection result of the present current value CJ of the current being supplied to the violet LED 31*a* by referring to the table data TE and increasing the brightness of the image data PG depending on the acquired signal output ratio SS and processing for reducing the brightness of the image data PV depending on the acquired signal output ratio SS is performed. Further, according to the present modification, each of the pixels included in the above-described region of interest AQ is subjected to either one of the processing using the foregoing numerical equation (9) and the processing using the foregoing numerical equation (10).

Accordingly, according to the present modification, even when a light-adjusting operation corresponding to an observation distance from the object has been performed in the special light observation mode, the color tone of the region containing hemoglobin such as a blood vessel and blood in the observation image to be displayed on the display apparatus 5 can be maintained to be a constant color tone. According to the present modification, even when the light-adjusting operation corresponding to the observation distance from the object has been performed in the special light observation mode, a color tone of a region containing no hemoglobin such as a connective tissue and a treatment instrument in the observation image to be displayed on the display apparatus 5 can be maintained to be a constant color tone. Therefore, according to the present modification, a burden on a user who diagnoses a lesion existing in a desired site within a living body while observing a capillary existing in a surface layer of a living tissue in the desired site can be reduced, for example.

The present invention is not limited to the above-described embodiment and modifications, but it goes without saying that various modifications and applications are possible without departing from the scope and gist of the invention.

What is claimed is:

1. An endoscope apparatus comprising:
  a light source that sequentially or simultaneously generates first narrow band light having an intensity within a predetermined wavelength range of a red range and second narrow band light having an intensity on a side of a longer wavelength than the predetermined wavelength range;
  an image pickup sensor configured to output an image pickup signal; and
  a processor comprising hardware, the processor being configured to:
    subject at least one of a first image obtained from the first narrow band light and a second image obtained from the second narrow band light to predetermined image processing and output at least one of the first image and the second image subjected to the predetermined image processing;
    generate an observation image using the first image and the second image obtained as a processing result of the predetermined image processing and output the generated observation image to a display; and
    perform control to acquire signal intensity information of the image pickup signal outputted from the image pickup sensor in response to irradiation of the object with the first narrow band light based on a detection result obtained by detecting a predetermined parameter representing a current operation state of a predetermined light source of the first narrow band light in the light source and further maintain a ratio of respective brightnesses of the first image and the second image used for generating the observation image to be a predetermined ratio based on the signal intensity information;
  wherein the processor acquires, as the signal intensity information, a signal output ratio calculated as a ratio of a signal intensity of an image pickup signal outputted from the image pickup sensor when the first narrow band light having an intensity within the predetermined wavelength range and having a center wavelength different from a predetermined center wavelength is irradiated onto the object to a reference signal intensity corresponding to a signal intensity of an image pickup signal outputted from the image pickup sensor when the first narrow band light having an intensity within the predetermined wavelength range and having the predetermined center wavelength is irradiated onto the object; and
  wherein the observation image is generated by subjecting the first image or the second image to the predetermined image processing, the predetermined image processing comprising performing color adjustment processing for suppressing a saturation of a region containing no hemoglobin in the first image or the second image based on the signal output ratio obtained in response to control by the processor and two color differences calculated using the first image and the second image.

2. The endoscope apparatus according to claim 1, wherein the one or more predetermined parameters include any of a present current value of a current supplied to the predetermined light source, a current temperature of the predetermined light source, and a current center wavelength of the first narrow band light emitted from the predetermined light source.

3. The endoscope apparatus according to claim 1, wherein the processor is further configured to:
  perform as color adjustment processing either one of processing for adjusting a brightness of the first image and processing for adjusting a brightness of the second image based on the signal output ratio obtained in response to the control by the processor, and
  perform the color correction processing for suppressing the saturation of the region containing no hemoglobin in the first image or the second image based on the signal output ratio obtained in response to the control by the processor and two color differences respectively calculated using the first image and the second image obtained as a processing result of the color adjustment processing, and
  generate the observation image using the first image and the second image subjected to the color adjustment processing and the color correction processing.

4. The endoscope apparatus according to claim 3, wherein the processor is configured to perform control to adjust a light amount of the first narrow band light emitted from the light source based on the signal output ratio instead of performing the color adjustment processing.

5. The endoscope apparatus according to claim 4, wherein the processor is further configured to change either a light emission time period of the predetermined light source or a current value of a current supplied to the predetermined light source, to adjust a light amount of the first narrow band light emitted from the light source.

6. The endoscope apparatus according to claim 3, wherein the processor is further configured to perform control to adjust an exposure time period when picking up an image of return light of the first narrow band light in the image pickup sensor based on the signal output ratio instead of performing the color adjustment processing.

7. The endoscope apparatus according to claim 3, wherein the processor is further configured to perform control to adjust a gain of an image pickup signal obtained by performing image pickup of return light of the first narrow band light in the image pickup sensor based on the signal output ratio instead of performing the color adjustment processing.

8. The endoscope apparatus according to claim 1, wherein the processor is further configured to:
  perform the color adjustment processing for suppressing the saturation of the region containing no hemoglobin in a processing target image while adjusting a brightness of the processing target image corresponding to either one of the first image and the second image based on the signal output ratio obtained in response to control by the processor and two color differences calculated using the first image and the second image, and
  generate the observation image using the first image and the second image subjected to the color adjustment processing.

9. A method of operating an endoscope apparatus, the method comprising:
  sequentially or simultaneously generating as illumination light first narrow band light as light having an intensity within a predetermined wavelength range of a red range in which a light absorption coefficient in a light absorption characteristic of hemoglobin sharply changes and second narrow band light as light having an intensity on a side of a longer wavelength than the predetermined wavelength range;
  picking up an image of return light from an object including a region containing hemoglobin irradiated with the illumination light and output an image pickup signal;
  subjecting at least one of a first image obtained by performing image pickup of the return light from the object irradiated with the first narrow band light and a second image obtained by performing image pickup of the return light from the object irradiated with the second narrow band light to predetermined image processing and outputting at least one of the first image and the second image subjected to the predetermined image processing;
  generating an observation image using the first image and the second image obtained as a processing result of the predetermined image processing and outputting the generated observation image to a display apparatus;
  acquiring signal intensity information of the image pickup signal in response to irradiation of the object with the first narrow band light based on a detection result of a predetermined parameter representing a current operation state of a predetermined light source of the first narrow band light; and
  performing control to maintain a ratio of respective brightnesses of the first image and the second image used for generating the observation image to be a predetermined ratio based on the signal intensity information;

wherein the acquiring acquires, as the signal intensity information, a signal output ratio calculated as a ratio of a signal intensity of an output image pickup signal when the first narrow band light having an intensity within the predetermined wavelength range and having a center wavelength different from a predetermined center wavelength is irradiated onto the object to a reference signal intensity corresponding to a signal intensity of an image pickup signal output when the first narrow band light having an intensity within the predetermined wavelength range and having the predetermined center wavelength is irradiated onto the object; and wherein the observation image is generated by subjecting the first image or the second image to the predetermined image processing, the predetermined image processing comprising performing color adjustment processing for suppressing a saturation of a region containing no hemoglobin in the first image or the second image based on the signal output ratio obtained in response the control and two color differences calculated using the first image and the second image.

10. An endoscope processor that is connected to an endoscope, the endoscope being configured to sequentially or simultaneously generating first narrow band light having an intensity within a predetermined wavelength range of a red range and second narrow band light having an intensity on a side of a longer wavelength than the predetermined wavelength range and the endoscope being configured to output an image pickup signal, wherein the processor is configured to:
  subject at least one of a first image obtained from the first narrow band light and a second image obtained from the second narrow band light to predetermined image processing and outputs at least one of the first image and the second image subjected to the predetermined image processing;
  generate an observation image using the first image and the second image obtained as a processing result of the predetermined image processing and output the generated observation image to a display; and
  perform control to acquire signal intensity information of the image pickup signal outputted from the endoscope in response to irradiation of the object with the first narrow band light based on a detection result obtained by detecting a predetermined parameter representing a current operation state of a predetermined light source of the first narrow band light in the light source apparatus and further maintain a ratio of respective brightnesses of the first image and the second image used for generating the observation image to be a predetermined ratio based on the signal intensity information;
  wherein the processor acquires, as the signal intensity information, a signal output ratio calculated as a ratio of a signal intensity of an image pickup signal outputted from the image pickup sensor when the first narrow band light having an intensity within the predetermined wavelength range and having a center wavelength different from a predetermined center wavelength is irradiated onto the object to a reference signal intensity corresponding to a signal intensity of an image pickup signal outputted from the image pickup sensor when the first narrow band light having an intensity within the predetermined wavelength range and having the predetermined center wavelength is irradiated onto the object; and wherein the observation image is generated by subjecting the first image or the second image to the predetermined image processing, the predetermined image processing comprising performing color adjustment processing for suppressing a saturation of a region containing no hemoglobin in the first image or the second image based on the signal output ratio obtained in response to control by the processor and two color differences calculated using the first image and the second image.

* * * * *